(12) United States Patent
Thomas et al.

(10) Patent No.: US 11,376,204 B2
(45) Date of Patent: Jul. 5, 2022

(54) COSMETIC COMPOSITION COMPRISING ANIONIC SURFACTANTS, AMPHOTERIC SURFAC-TANTS, CATIONIC POLYMERS AND LIQUID FATTY SUBSTANCES CHOSEN FROM FATTY ALCO-HOLS AND FATTY ESTERS, AND COSMETIC TREATMENT PROCESS

(71) Applicant: L'OREAL, Paris (FR)

(72) Inventors: Béatrice Thomas, Saint-Ouen (FR); Françoise Pataut, Clichy (FR); Véronique Modeste, Saint-Ouen (FR)

(73) Assignee: L'OREAL, Paris (FR)

( * ) Notice: Subject to any disclaimer, the term of this patent is extended or adjusted under 35 U.S.C. 154(b) by 622 days.

(21) Appl. No.: 16/301,635

(22) PCT Filed: May 15, 2017

(86) PCT No.: PCT/EP2017/061623
§ 371 (c)(1),
(2) Date: Nov. 14, 2018

(87) PCT Pub. No.: WO2017/198624
PCT Pub. Date: Nov. 23, 2017

(65) Prior Publication Data
US 2019/0282481 A1    Sep. 19, 2019

(30) Foreign Application Priority Data

May 18, 2016 (FR) .................................... 16 54423

(51) Int. Cl.
| | |
|---|---|
| *A61K 8/46* | (2006.01) |
| *A61K 8/34* | (2006.01) |
| *A61K 8/37* | (2006.01) |
| *A61K 8/44* | (2006.01) |
| *A61Q 5/02* | (2006.01) |
| *A61Q 5/12* | (2006.01) |
| *A61K 8/81* | (2006.01) |

(52) U.S. Cl.
CPC .............. *A61K 8/463* (2013.01); *A61K 8/342* (2013.01); *A61K 8/37* (2013.01); *A61K 8/442* (2013.01); *A61K 8/466* (2013.01); *A61K 8/817* (2013.01); *A61Q 5/02* (2013.01); *A61Q 5/12* (2013.01); *A61K 2800/262* (2013.01); *A61K 2800/34* (2013.01); *A61K 2800/5426* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 6,849,584 | B2 | 2/2005 | Geary et al. |
| 2003/0106167 | A1 | 6/2003 | Rose et al. |
| 2005/0158269 | A1 | 7/2005 | Simonet |
| 2009/0169644 | A1* | 7/2009 | Goddinger ............. A61K 8/922 424/642 |
| 2010/0249004 | A1* | 9/2010 | Fack ........................ A61K 8/55 510/124 |
| 2011/0213139 | A1 | 9/2011 | Chan et al. |
| 2012/0247498 | A1 | 10/2012 | Mathonneau |
| 2015/0093348 | A1 | 4/2015 | Sato et al. |

FOREIGN PATENT DOCUMENTS

| | | |
|---|---|---|
| CA | 2148944 A1 | 5/1994 |
| CN | 101411676 A | 4/2009 |
| DE | 103 54 116 A1 | 6/2005 |
| DE | 10 2013 225 609 A1 | 6/2014 |
| EP | 1 604 639 A1 | 12/2005 |
| FR | 2 984 161 A1 | 6/2013 |
| JP | 2001-131580 A | 5/2001 |
| JP | 2002-536311 A | 10/2002 |
| JP | 2005-232169 A | 9/2005 |
| JP | 2006-249096 A | 9/2006 |
| WO | WO 92/05767 A1 | 4/1992 |
| WO | WO 00/45781 A1 | 8/2000 |
| WO | WO 2006/013036 A1 | 2/2006 |
| WO | WO 2006/136303 A1 | 12/2006 |

(Continued)

OTHER PUBLICATIONS

International Search Report dated Jul. 28, 2017 in PCT/EP2017/061623 Filed on May 15, 2017.
Database GNPD Mintel, "Silicone-Free Repairing Shampoo Gel", Mar. 1, 2016, XP002762341, 2 pages.
Database GNPD Mintel, "Shampoo", Apr. 1, 2016, XP002771739, 3 pages.
Japanese Office Action dated Sep. 2, 2019, in Patent Application No. 2018-553153, 4 pages.
Combined Chinese Office Action and Search Report dated Dec. 17, 2020 in corresponding Chinese Patent Application No. 201780029607.4 (with English Translation of Category of Cited Documents), 9 pages.
Rhodia: Miracare SLB-365, 2013, SdT Art. 54 (2), 11 pages.

(Continued)

*Primary Examiner* — Robert A Wax
*Assistant Examiner* — Randeep Singh
(74) *Attorney, Agent, or Firm* — Oblon, McClelland, Maier & Neustadt, L.L.P.

(57) ABSTRACT

Cosmetic composition comprising anionic surfactants, amphoteric surfactants, cationic polymers and liquid fatty substances chosen from fatty alcohols and fatty esters, and cosmetic treatment process The present invention relates to a cosmetic composition, especially a hair composition, comprising: —one or more anionic surfactants, —one or more amphoteric surfactants, —one or more cationic polymers with a high cationic charge density, —one or more liquid fatty substances chosen from non-oxyalkylenated fatty alcohols and monocarboxylic fatty acid esters, and also mixtures thereof. The invention also relates to a cosmetic process for treating, and more particularly for washing and conditioning, keratin materials, especially the hair, using the present composition.

21 Claims, No Drawings

(56) References Cited

FOREIGN PATENT DOCUMENTS

WO    WO 2011/073564  A2    6/2011
WO    WO 2013/092608  A2    6/2013

OTHER PUBLICATIONS

Wikipedia: Sodium lauroamphoacetate, [retrieved on Jan. 20, 2021] Retrieved from the Internet <URL: https://en/wikipedia.org/w/index.php?title=Sodium_laurophoacetate&olid=1001555476>, 2 pages.
Nalco: Personal Care Polymers, 1 page.
Texapon® NSO, 2000, 1 page.
Cognis: Lorol Technisch, 2004, 1 page.
Rohdia: Miranol® C2M-SF CONC, 2005, 2 pages.

* cited by examiner

COSMETIC COMPOSITION COMPRISING ANIONIC SURFACTANTS, AMPHOTERIC SURFAC-TANTS, CATIONIC POLYMERS AND LIQUID FATTY SUBSTANCES CHOSEN FROM FATTY ALCO-HOLS AND FATTY ESTERS, AND COSMETIC TREATMENT PROCESS

The present invention relates to a cosmetic composition comprising at least one anionic surfactant, at least one amphoteric surfactant, at least one cationic polymer with a high cationic charge density and at least one liquid fatty substance chosen from certain fatty alcohols and certain fatty esters, and to a cosmetic treatment process using this composition. These compositions are more particularly intended for washing keratin materials, especially the hair.

It is well known that hair may be sensitized or embrittled to varying degrees as a result of the action of atmospheric agents such as light, water and moisture, and also repeated mechanical or chemical treatments such as brushing, combing, washing, bleaching, permanent waving, relaxing and/or dyeing. These attacking factors impair the hair fibre and reduce its mechanical properties such as the tensile strength, the breaking load and the elasticity, or its resistance to swelling in an aqueous medium. The hair is dull, coarse and brittle. The hair is difficult to disentangle and to style.

Substances for protecting the hair against such degradation have been sought for many years in the cosmetics industry; products that improve the cosmetic properties, especially the disentangling, softness, smoothness and sheen, and that preserve or reinforce the intrinsic mechanical properties of keratin fibres, such as the tensile strength, the breaking load and the elasticity, or their resistance to swelling in an aqueous medium, are sought in particular.

Thus, shampoos have been proposed, especially for sensitized hair, which combine a cationic polymer and a silicone, to obtain acceptable cosmetic performance qualities.

However, these compositions have several drawbacks: presence of silicone, the environmental profile (biodegradability, water footprint) of which is not always optimal, generally opaque appearance of the shampoo associated with the presence of silicone, start of foaming and foam quality that are judged as being insufficient, and rapid regreasing of the hair accompanied by lankness.

In addition, repeated applications of these compositions often have the effect of giving the hair an unpleasant feel, loss of volume and liveliness of the head of hair, and occasionally loss of sheen.

The interest in developing a shampoo that is advantageously silicone-free and clear, having improved working qualities and good cosmetic performance qualities, and that can thus be used to give good conditioning properties to the hair, in particular to sensitized, embrittled or damaged hair, and also to fine hair, thus arose from these observations.

One subject of the present invention is a cosmetic composition, especially a hair composition, comprising:
- one or more anionic surfactants,
- one or more amphoteric surfactants,
- one or more cationic polymers with a cationic charge density of greater than or equal to 4 meq./g,
- one or more liquid fatty substances chosen from non-oxyalkylenated alcohols comprising at least 8 carbon atoms, monocarboxylic acid esters comprising at least 8 carbon atoms, and mixtures thereof.

It has been found that, with the compositions according to the invention, the hair, even damaged hair, has improved softness, suppleness and smoothness; it is easy to disentangle; the hair also appears to be more coated, which is most particularly appreciable in the case of damaged hair, which then appears more natural, healthy and in good condition, with less apparent frizziness.

The compositions according to the invention afford nutrition to the hair, especially sensitized hair, and also lightness, which will lead to easier shaping of the head of hair.

These properties may be obtained while avoiding the addition of silicone to the composition according to the invention; thus, preferably, the composition according to the invention does not comprise any silicones (less than 0.1% by weight, especially 0%).

It is also possible, by virtue of the invention, to obtain a composition that has good working qualities, and especially rapid starting of foaming with good foam abundance.

By virtue of the invention, it is also possible to conserve the clarity of shampoo compositions, even when they contain a highly charged cationic polymer, and liquid fatty substances in a high content.

Thus, advantageously, the composition according to the invention is transparent; the term "transparent composition" means a composition through which it is possible to see distinctly with the naked eye.

In particular, the composition according to the invention may have a turbidity value of less than or equal to 200 NTU units, better still less than 100 NTU units, preferentially less than 50 NTU units, in particular less than 20 NTU units and even more particularly less than 10 NTU units.

The turbidity may be measured according to the NTU method, using a 2100P model turbidimeter from the company Hach Co., at room temperature and pressure (25° C. and 1 atm.).

The composition may also be characterized by measuring its transmittance, which is measured using a Cary 100 model spectrophotometer from the company Varian, at room temperature and pressure (25° C., 1 atm.), at a wavelength of 700 nm.

The transmittance of the compositions according to the invention is preferably greater than or equal to 96%.

In the present description, the expression "at least one" is equivalent to the expression "one or more" and can substitute for said expression; the expression "between" is equivalent to the expression "ranging from" and can substitute for said expression, which implies that the limits are included.

1/ Anionic Surfactants

The composition according to the invention thus comprises one or more anionic surfactants.

The term "anionic surfactant" means a surfactant comprising, as ionic or ionizable groups, only anionic groups. These anionic groups are preferably chosen from the $CO_2H$, $CO_2^-$, $SO_3H$, $SO_3^-$, $OSO_3H$, $OSO_3^-$, $-H_2PO_3$, $-HPO_3^-$, $-PO_3^{2-}$, $-H_2PO_2$, $=HPO_2$, $-HPO_2^-$, $=PO_2^-$, $=POH$ or $=PO^-$ groups.

Preferably, the anionic surfactants are chosen from sulfate, sulfonate and carboxylate anionic surfactants, alone or as a mixture.

For the purposes of the present invention, the term "carboxylate anionic surfactant" means an anionic surfactant comprising one or more carboxylic or carboxylate functions ($-COOH$ or $-COO^-$), and which may optionally also comprise one or more sulfonate and/or sulfate functions.

The term "sulfonate anionic surfactant" means an anionic surfactant comprising one or more sulfonate functions ($-SO_3H$ or $-SO_3^-$), and not comprising any carboxylic or carboxylate functions ($-COOH$ or $-COO^-$).

The sulfate or sulfonate anionic surfactants that may be used in the composition according to the invention may be chosen from alkyl sulfates, alkyl ether sulfates, alkylamido ether sulfates, alkylaryl polyether sulfates, monoglyceride sulfates, alkylsulfonates, alkylamidesulfonates, alkylarylsulfonates, alpha-olefin sulfonates, paraffin sulfonates, acylisethionates, N-acyltaurates, N-methyl-N-acyltaurates, and the corresponding acid forms, the alkyl and acyl groups of all these compounds preferably comprising from 6 to 30 carbon atoms, better still from 12 to 24, or even from 16 to 22 carbon atoms, and the aryl group preferably denoting a phenyl or benzyl group.

The sulfate or sulfonate anionic surfactants may be oxyalkylenated and then preferably comprise from 1 to 50 ethylene oxide units and better still from 2 to 10 ethylene oxide units.

Preferably, the composition comprises one or more sulfate or sulfonate anionic surfactants chosen, the salts being included, from:
  C6-C30, especially C12-C24 or even C12-C20 alkyl sulfates,
  C6-C30, especially C12-C24 or even C12-C20 alkyl ether sulfates, preferably comprising from 2 to 20 ethylene oxide units, and
  C6-C30, especially C12-C24 or even C12-C20 acylisethionates.

The carboxylate anionic surfactants that may be used may be chosen from alkyl sulfosuccinates, alkyl ether sulfosuccinates, alkylamide sulfosuccinates, acyl glycinates, acylsarcosinates and acyl glutamates, and the corresponding acid forms, the alkyl and/or acyl groups of these compounds comprising from 6 to 30 carbon atoms, better still from 12 to 24, or even from 16 to 22 carbon atoms. Use may also be made of alkyl monoesters of polyglycoside-polycarboxylic acids such as alkyl polyglycoside citrates, alkyl polyglycoside tartrates and alkyl polyglycoside sulfosuccinates, and alkylsulfosuccinamates, the alkyl or acyl group of these compounds comprising from 6 to 30 carbon atoms, better still from 12 to 24, or even from 16 to 22 carbon atoms; use may also be made of the salts thereof. Use may also be made of acyllactylates, the acyl group of which comprises from 6 to 30 carbon atoms, better still from 8 to 20 carbon atoms, or even from 12 to 24 carbon atoms.

Mention may also be made of alkyl-D-galactosideuronic acids, and also polyoxyalkylenated ether carboxylic acids, such as polyoxyalkylenated (C8-C30)alkyl ether carboxylic acids, polyoxyalkylenated (C14-C30)alkyl(C6-C30)aryl ether carboxylic acids, polyoxyalkylenated (C14-C30)alkylamido ether carboxylic acids; and also the salts of all these compounds; the compounds preferably comprising from 2 to 50 ethylene oxide units; and also mixtures thereof.

These anionic surfactants may all be oxyalkylenated and then preferably comprise from 1 to 50 ethylene oxide units and better still from 2 to 10 ethylene oxide units.

The anionic surfactants of the polyoxyalkylenated alkyl ether carboxylic acid, or salt, type are in particular those corresponding to formula (A):

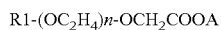

in which:
  R1 represents a linear or branched C8-C30, especially C8-C22, alkyl or alkenyl radical, an alkyl(C8-C9) phenyl radical, or a radical R2CONH—CH2-CH2- with R2 denoting a linear or branched C9-C21 alkyl or alkenyl radical;
  n is an integer or decimal number (average value) that may range from 2 to 24 and preferably from 2 to 10,
  A denotes H, ammonium, Na, K, Li, Mg or a monoethanolamine or triethanolamine residue.

The polyoxyalkylenated alkyl ether carboxylic acids are preferably chosen from those of formula (A) in which:
  R1 denotes a linear or branched C8-C22, especially C10-C16 or even C12-C14 alkyl radical, or alternatively a (C8-C9)alkylphenyl radical; and
  n ranges from 2 to 20 or even from 2 to 10, and
  A denotes a hydrogen or sodium atom.

Preferably, the composition comprises one or more carboxylate anionic surfactants chosen, the salts being included, from:
  C6-C24 and especially C12-C20 acylglutamates;
  C6-C24 and especially C12-C20 acylsarcosinates;
  C6-C24 and especially C12-C20 acyllactylates;
  C6-C24 and especially C12-C20 alkylsulfosuccinates, and
  polyoxyalkylenated (C6-C24)alkyl ether carboxylic acids and salts thereof, polyoxyalkylenated (C6-C24)alkylamido ether carboxylic acids and salts thereof; in particular those comprising from 2 to 15 alkylene oxide groups.

The salified forms are in particular alkali metal salts such as sodium salts, ammonium salts, amine salts, amino alcohol salts or alkaline-earth metal salts, for example magnesium salts. Alkali metal or alkaline-earth metal salts and in particular the sodium or magnesium salts are preferably used.

Preferentially, the composition according to the invention comprises one or more anionic surfactants chosen, alone or as a mixture, from:
  C6-C30, especially C12-C24 or even C12-C20 alkyl sulfates;
  C6-C30, especially C12-C24 or even C12-C20 alkyl ether sulfates; preferably comprising from 2 to 20 ethylene oxide units,
  C6-C30, especially C12-C24 or even C12-C20 alkylsulfosuccinates;
  C6-C30, especially C12-C24 or even C12-C20 alkyl ether sulfosuccinates; preferably comprising from 2 to 20 ethylene oxide units,
  C6-C30, especially C12-C24 or even C12-C20 alkylsulfoacetates;
  polyoxyalkylenated (C6-C24)alkyl ether carboxylic acids, in particular those comprising from 2 to 15 alkylene oxide groups;
  polyoxyalkylenated (C6-C24)alkylamido ether carboxylic acids, in particular those comprising from 2 to 15 alkylene oxide groups;
  and also the salts of all these compounds.

According to a particular embodiment of the invention, the composition comprises:
  at least one anionic surfactant chosen from C6-C30, especially C12-C24 or even C12-C20 alkyl ether sulfates, preferably comprising from 2 to 20 ethylene oxide units, and
  at least one anionic surfactant chosen from C6-C30, especially C12-C24 or even C12-C20 alkyl ether sulfosuccinates, preferably comprising from 2 to 20 ethylene oxide units.

According to another particular embodiment of the invention, the composition comprises:
  at least one anionic surfactant chosen from C6-C30, especially C12-C24 or even C12-C20 alkyl ether sulfates, preferably comprising from 2 to 20 ethylene oxide units, at least one anionic surfactant chosen from C6-C30, especially C12-C24 or even C12-C20 alkyl ether sulfosuccinates, preferably comprising from 2 to 20 ethylene oxide units, and at least one anionic surfactant chosen from C6-C30, especially C12-C24 or even C12-C20 alkylsulfoacetates.

The composition according to the invention preferably comprises said anionic surfactant(s) in a total amount ranging from 2% to 40% by weight, preferably from 3% to 30% by weight, better still from 5% to 20% by weight and preferentially from 7% to 15% by weight, relative to the total weight of the composition.

2/ Amphoteric Surfactants

The composition according to the invention also comprises one or more amphoteric surfactants.

The amphoteric surfactants that may be used in the invention may be derivatives of optionally quaternized secondary or tertiary aliphatic amines containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of (C8-C20)alkylbetaines, sulfobetaines, alkyl(C8-C20)sulfobetaines, (C8-C20)alkylamido(C1-C6)alkylbetaines, such as cocamidopropylbetaine, and (C8-C20)alkylamido(C1-C6)alkylsulfobetaines.

Among the optionally quaternized secondary or tertiary aliphatic amine derivatives that may be used, mention may be made of the compounds of formulae (A1) and (A2) below:

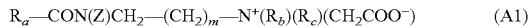

in which:

$R_a$ represents a $C_{10}$-$C_{30}$ alkyl or alkenyl group derived from an acid $R_a$—COOH preferably present in hydrolysed coconut oil, or a heptyl, nonyl or undecyl group, $R_b$ represents a β-hydroxyethyl group, $R_c$ represents a carboxymethyl group;

m is equal to 0, 1 or 2,

Z represents a hydrogen atom or a hydroxyethyl or carboxymethyl group,

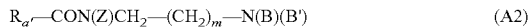

in which:

B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom, B' represents —(CH$_2$)$_z$—Y', with z=1 or 2, and Y' representing —COOH, —COOZ', —CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion derived from an alkali metal or alkaline-earth metal, such as sodium, potassium or magnesium; an ammonium ion; or an ion derived from an organic amine and especially from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane; and $R_a$, represents a C10-C30 alkyl or alkenyl group of an acid $R_a$,COOH preferably present in hydrolysed linseed oil or coconut oil, an alkyl group, in particular a $C_{17}$ alkyl group, and its iso form, or an unsaturated $C_{17}$ group.

Among these two structures, the compounds corresponding to formula (A2) are preferred.

These compounds are classified in the CTFA dictionary, 5$^{th}$ edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

Examples that may be mentioned include the cocoamphodiacetate sold by the company Rhodia under the trade name Miranol® C2M Concentrate or under the trade name Miranol Ultra C 32 and the product sold by the company Chimex under the trade name Chimexane HA.

Use may also be made of compounds of formula (A3):

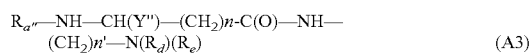

in which:

$R_{a''}$ represents a 010-C30 alkyl or alkenyl group derived from an acid $R_{a'''}$—C(O)OH, which is preferably present in hydrolysed linseed oil or coconut oil;

Y" represents the group —C(O)OH, —C(O)OZ", —CH$_2$—CH(OH)—SO$_3$H or the group —CH$_2$—CH(OH)—SO$_3$—Z", with Z" representing a cationic counterion derived from an alkali metal or alkaline-earth metal, such as sodium, an ammonium ion or an ion derived from an organic amine;

$R_d$ and $R_e$, independently of each other, represent a C1-C4 alkyl or hydroxyalkyl radical; and n and n', independently of each other, denote an integer ranging from 1 to 3.

Mention may be made especially of the compound classified in the CTFA dictionary under the name sodium diethylaminopropyl cocoaspartamide and sold by the company Chimex under the name Chimexane HB.

Preferably, the amphoteric surfactants are chosen from (C8-C20)alkylbetaines, (C8-C20)alkylamido(C1-C6)alkylbetaines and (C8-C20)alkylamphodiacetates, and mixtures thereof; and more particularly from (C8-C20)alkylbetaines and (C8-C20)alkylamido(C1-C6)alkylbetaines and mixtures thereof.

The composition according to the invention preferably comprises said amphoteric surfactant(s) in an amount ranging from 1% to 25% by weight, preferably from 5% to 20% by weight and better still from 8% to 18% by weight, relative to the total weight of the composition.

Preferably, the composition according to the invention comprises one or more anionic surfactants and one or more amphoteric surfactants in a total amount such that the weight ratio between anionic surfactant(s) and amphoteric surfactant(s) is less than or equal to 1, preferably between 0.01 and 1, especially between 0.10 and 0.95 and better still between 0.45 and 0.85.

3/ Cationic Polymers

The composition according to the invention also comprises one or more cationic polymers with a cationic charge density of greater than or equal to 4 milliequivalents/gram (meq./g), preferably with a cationic charge density of greater than or equal to 5 meq./g; especially with a cationic charge density of between 4 and 12 meq./g, preferably between 5 and 8 meq./g.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their molar proportion or weight proportion. It may also be determined experimentally by the Kjeldahl method.

For the purposes of the present invention, the term "cationic polymer" denotes any polymer comprising cationic groups and/or groups that can be ionized into cationic groups.

The cationic polymers with a cationic charge density of greater than or equal to 4 meq./g may be chosen from those containing units comprising primary, secondary, tertiary and/or quaternary amine groups, which may either form part of the main polymer chain or be borne by a side substituent directly attached thereto. The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) Homopolymers or copolymers derived from acrylic or methacrylic esters or amides and comprising at least one of the units of the following formulae:

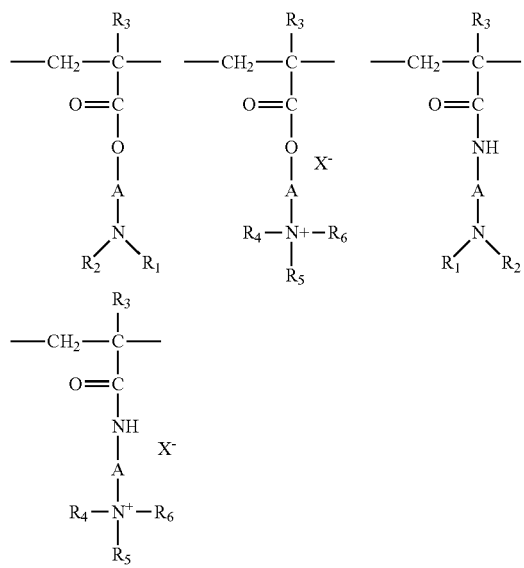

in which:
R3, which may be identical or different, denote a hydrogen atom or a $CH_3$ radical;
A, which may be identical or different, represent a linear or branched divalent alkyl group of 1 to 6 carbon atoms, preferably 2 or 3 carbon atoms, or a hydroxyalkyl group of 1 to 4 carbon atoms;
R4, R5 and R6, which may be identical or different, represent an alkyl group containing from 1 to 18 carbon atoms or a benzyl radical, preferably an alkyl group containing from 1 to 6 carbon atoms;
$R_1$ and $R_2$, which may be identical or different, represent a hydrogen atom or an alkyl group containing from 1 to 6 carbon atoms, preferably methyl or ethyl;
X denotes an anion derived from a mineral or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), mention may be made of:
copolymers of acrylamide and of dimethylaminoethyl methacrylate quaternized with dimethyl sulfate or with a dimethyl halide, such as that sold under the name Hercofloc by the company Hercules,
copolymers of acrylamide and of methacryloyloxyethyltrimethylammonium chloride, such as the products sold under the name Bina Quat P 100 by the company Ciba Geigy,
the copolymer of acrylamide and of methacryloyloxyethyltrimethylammonium methosulfate, such as that sold under the name Reten by the company Hercules,
quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573;
dimethylaminoethyl methacrylate/vinylcaprolactam/vinylpyrrolidone terpolymers, such as the products sold under the name Gaffix VC 713 by the company ISP,
vinylpyrrolidone/methacrylamidopropyldimethylamine copolymers, such as the products sold under the name Styleze CC 10 by ISP,
quaternized vinylpyrrolidone/dimethylaminopropylmethacrylamide copolymers such as the product sold under the name Gafquat HS 100 by the company ISP,
preferably crosslinked polymers of methacryloyloxy(C1-C4)alkyltri(C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) Cationic polysaccharides, especially cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are defined especially in the CTFA dictionary as hydroxyethylcellulose quaternary ammoniums that have reacted with an epoxide substituted with a trimethylammonium group. Among the cationic cellulose copolymers or cellulose derivatives grafted with a water-soluble quaternary ammonium monomer, mention may be made of hydroxyalkylcelluloses grafted especially with a methacryloylethyltrimethylammonium, methacrylamidopropyltrimethylammonium or dimethyldiallylammonium salt. Among the cationic galactomannan gums, mention may be made of guar gums comprising trialkylammonium cationic groups.

(3) Polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bishaloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyaminoamide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by Hercules Inc. or else under the name PD 170 or Delsette 101 by Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

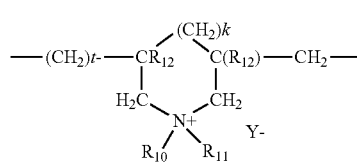

(I)

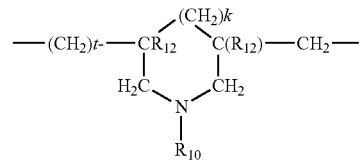

(II)

in which
k and t are equal to 0 or 1, the sum k+t being equal to 1;
R12 denotes a hydrogen atom or a methyl radical;
R10 and R11, independently of each other, denote a C1-C6 alkyl group, a C1-C5 hydroxyalkyl group, a C1-C4 amidoalkyl group; or alternatively R10 and R11 may denote, together with the nitrogen atom to which they are attached, a heterocyclic group such as piperidyl or morpholinyl; R10 and R11, independently of each other, preferably denote a C1-C4 alkyl group;
$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco, and the copolymers of diallyldimethylammonium salts (for example chloride) and of acrylamide.

(8) Quaternary diammonium polymers comprising repeating units of formula:

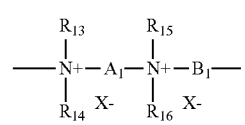

(III)

in which:
R13, R14, R15 and R16, which may be identical or different, represent aliphatic, alicyclic or arylaliphatic radicals comprising from 1 to 20 carbon atoms or C1-C12 hydroxyalkyl aliphatic radicals,
or else R13, R14, R15 and R16, together or separately, form, with the nitrogen atoms to which they are attached, heterocycles optionally comprising a second non-nitrogen heteroatom;
or else R13, R14, R15 and R16 represent a linear or branched C1-C6 alkyl radical substituted with a nitrile, ester, acyl, amide or —CO—O—R17-D or —CO—NH—R17-D group, where R17 is an alkylene and D is a quaternary ammonium group;
A1 and B1 represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and
$X^-$ denotes an anion derived from a mineral or organic acid;
it being understood that A1, R13 and R15 can form, with the two nitrogen atoms to which they are attached, a piperazine ring;
in addition, if A1 denotes a linear or branched, saturated or unsaturated alkylene or hydroxyalkylene radical, B1 may also denote a group (CH2)n-CO-D-OC(CH2)p- with n and p, which may be identical or different, being integers ranging from 2 to 20, and D denoting:
- a) a glycol residue of formula —O—Z—O—, in which Z denotes a linear or branched hydrocarbon-based radical, or a group corresponding to one of the following formulae: —(CH2CH2O)x-CH2CH2- and —[CH2CH(CH3)O]y-CH2CH(CH3)-, in which x and y denote an integer from 1 to 4, representing a defined and unique degree of polymerization or any number from 1 to 4 representing an average degree of polymerization;
- b) a bis-secondary diamine residue, such as a piperazine derivative;
- c) a bis-primary diamine residue of formula —NH—Y—NH—, in which Y denotes a linear or branched hydrocarbon-based radical, or else the divalent radical —CH2-CH2-S—S—CH2-CH2-;
- d) a ureylene group of formula —NH—CO—NH—.

Preferably, X⁻ is an anion, such as chloride or bromide. These polymers have a number-average molar mass (Mn) generally of between 1000 and 100 000.

Mention may be made more particularly of polymers that are composed of repeating units corresponding to the formula:

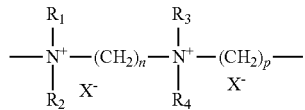

(IV)

in which R1, R2, R3 and R4, which may be identical or different, denote an alkyl or hydroxyalkyl radical containing from 1 to 4 carbon atoms, n and p are integers ranging from 2 to 20 approximately, and X— is an anion derived from a mineral or organic acid.

A particularly preferred compound of formula (IV) is the one for which R1, R2, R3 and R4 represent a methyl radical and n=3, p=6 and X=Cl, known as Hexadimethrine chloride according to the INCI (CTFA) nomenclature.

(9) Polyquaternary ammonium polymers comprising units of formula (V):

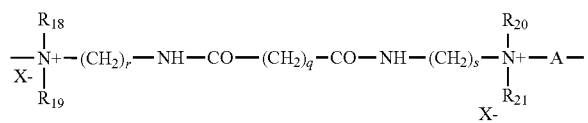

(V)

in which:
- R18, R19, R20 and R21, which may be identical or different, represent a hydrogen atom or a methyl, ethyl, propyl, β-hydroxyethyl, β-hydroxypropyl or —CH2CH2(OCH2CH2)pOH radical, in which p is equal to 0 or to an integer between 1 and 6, with the proviso that R18, R19, R20 and R21 do not simultaneously represent a hydrogen atom,
- r and s, which may be identical or different, are integers between 1 and 6,
- q is equal to 0 or to an integer between 1 and 34,
- X⁻ denotes an anion such as a halide,
- A denotes a divalent dihalide radical or preferably represents —CH2-CH2-O—CH2-CH2-.

Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the product sold under the name Luviquat® Excellence by the company BASF.

(11) Polyamines such as Polyquart® H sold by Cognis, referred to under the name Polyethylene glycol (15) tallow polyamine in the CTFA dictionary.

(12) Polymers comprising in their structure:
(a) one or more units corresponding to formula (A) below:

(A)

(b) optionally one or more units corresponding to formula (B) below:

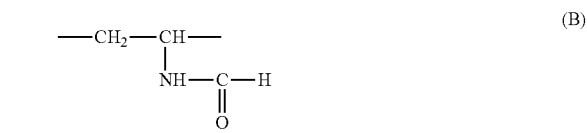

(B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to the formula (A) and from 0 mol % to 95 mol % of units corresponding to the formula (B), preferably from 10 mol % to 100 mol % of units corresponding to the formula (A) and from 0 mol % to 90 mol % of units corresponding to the formula (B).

These polymers may be obtained, for example, by partial hydrolysis of polyvinylformamide. This hydrolysis may take place in acidic or basic medium.

The weight-average molecular mass of said polymer, measured by light scattering, may range from 1000 to 3 000 000 g/mol, preferably from 10 000 to 1 000 000 and more particularly from 100 000 to 500 000 g/mol.

The polymers comprising units of formula (A) and optionally units of formula (B) are sold in particular under the Lupamin name by BASF, such as, for example, in a non-limiting way, the products provided under the names Lupamin 9095, Lupamin 5095, Lupamin 1095, Lupamin 9030 (or Luviquat 9030) and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the composition comprises at least one cationic polymer with a cationic charge density of greater than or equal to 4 meq./g, chosen from those of families (1), (7) and (10) mentioned above; and in particular chosen from:
preferably crosslinked polymers of methacryloyloxy(C1-C4)alkyltri(C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide; and in particular crosslinked copolymers of acrylamide/methacryloyloxyethyltrimethylammonium chloride and crosslinked homopolymers of methacryloyloxyethyltrimethylammonium chloride;

homopolymers of dimethyldiallylammonium salts (for example chloride), and copolymers of diallyldimethylammonium salts (for example chloride) and of acrylamide;

quaternary polymers of vinylpyrrolidone and of vinylimidazole;

optionally crosslinked homopolymers or copolymers of methacryloyloxy(C1-C4)alkyltri(C1-C4)alkylammonium salts; and mixtures thereof.

Preferentially, the composition comprises at least one cationic polymer with a cationic charge density of greater than or equal to 4 meq./g, chosen from homopolymers of dimethyldiallylammonium salts (for example chloride).

The composition according to the invention may comprise the cationic polymer(s) with a cationic charge density of greater than or equal to 4 meq./g in an amount ranging from 0.01% to 10% by weight, or even from 0.05% to 5% by weight, better still from 0.1% to 2% by weight, and even better still from 0.2% to 1% by weight, relative to the total weight of the composition.

4/ Liquid Fatty Substances

The composition according to the invention also comprises one or more liquid fatty substances, chosen from:
non-oxyalkylenated alcohols comprising at least 8 carbon atoms,
monocarboxylic acid esters comprising at least 8 carbon atoms in total, and
mixtures thereof.

The term "liquid" refers to a compound that is liquid at room temperature and at atmospheric pressure (25° C., 1 atm.), preferably with a viscosity of less than or equal to 2 Pa·s, better still less than or equal to 1 Pa·s and even better still less than or equal to 0.1 Pa·s at a temperature of 25° C., 1 atm. and at a shear rate of $1\ s^{-1}$.

The liquid alcohols according to the present invention are non-oxyalkylenated and comprise at least 8 carbon atoms. They preferably have the following structure: R—OH in which R denotes a linear or branched alkyl or alkenyl group comprising at least 8 carbon atoms, preferably from 8 to 30 carbon atoms, better still from 10 to 24 carbon atoms and even better still from 12 to 22 carbon atoms, R possibly being substituted with one or more hydroxyl groups.

The unsaturated liquid fatty alcohols contain in their structure at least one double or triple bond, and preferably one or more double bonds. When several double bonds are present, there are preferably 2 or 3 of them, and they may be conjugated or unconjugated. These unsaturated fatty alcohols may be linear or branched.

Preferably, R denotes a saturated, branched C8-C30, especially C10-C24 and better still C12-C24 alkyl group, or a linear or branched, especially linear, C8-C30, especially C10-C24 and better still C12-C24 alkenyl group comprising 1 to 3 double bonds (C═C), preferably only one double bond.

As alcohol that may be used in the context of the invention, mention may be made especially of oleyl alcohol, linoleyl alcohol, linolenyl alcohol, undecylenyl alcohol, isocetyl alcohol, isostearyl alcohol, 2-octyl-1-dodecanol, 2-butyloctanol, 2-hexyl-1-decanol, 2-decyl-1-tetradecanol and 2-tetradecyl-1-cetanol, and mixtures thereof. Preferentially, the alcohols are chosen from 2-octyl-1-dodecanol and 2-decyl-1-tetradecanol, and also mixtures thereof.

The liquid fatty esters that may be used are esters of monoalcohols or of polyols with monocarboxylic acids. Said esters comprise at least 8 carbon atoms in total. Preferably, they comprise from 8 to 32 carbon atoms in total, especially from 10 to 30 carbon atoms in total, in particular from 12 to 24 carbon atoms in total. Preferably, the monocarboxylic acids comprise from 3 to 32 carbon atoms, especially from 5 to 30 carbon atoms and better still from 8 to 24 carbon atoms in total.

Preferably, they are linear or branched and may be saturated or unsaturated.

Preferably, the alcohols comprise from 1 to 32 carbon atoms in total, especially from 2 to 30 carbon atoms and better still from 2 to 24 carbon atoms in total. Preferably, they are linear or branched and may be saturated or unsaturated. Preferably, they comprise 1 to 4 hydroxyl groups (OH).

Preferably, at least one of the alcohols and/or monoacids comprises at least one chain of more than 7 carbon atoms, better still more than 8 carbon atoms.

For the esters of monoalcohols, preferably at least one from among the alcohol and the acid from which the esters of the invention are obtained is branched.

Preferably, the liquid fatty ester according to the invention is chosen from esters of a fatty acid and of a mono alcohol.

Most particularly, use may be made of esters of a C6-C24 monocarboxylic acid and of a C2-C20 alcohol, at least one from among the acid and the alcohol being branched or unsaturated. Even more preferentially, use may be made of esters of a C12-C24 monocarboxylic acid and of a C2-C10 alcohol, at least one from among the acid and the alcohol being branched or unsaturated.

Mention may be made of:
C2-C20 alkyl myristates, especially ethyl myristate, isopropyl myristate, 2-octyldodecyl myristate, isooctyl myristate or isododecyl myristate;
C2-C20 alkyl palmitates, and especially ethyl palmitate, isopropyl palmitate, 2-ethylhexyl palmitate or 2-octyldecyl palmitate,
isocetyl stearate, 2-ethylhexyl isononanoate, isononyl isononanoate, isostearyl isononanoate, 2-hexyldecyl laurate, stearyl octanoate, isopropyl lanolate, isodecyl neopentanoate, isostearyl neopentanoate, and
mixtures thereof.

Preferentially, use may be made of isopropyl myristate or isononyl isononanoate, and mixtures thereof.

The composition according to the invention may comprise the liquid fatty substance(s), chosen from the alcohols and esters defined above, in a total amount ranging from 0.01% to 20% by weight, or even from 0.1% to 10% by weight, better still from 0.5% to 5% by weight, and even better still from 0.7% to 2% by weight, relative to the total weight of the composition.

In a particular embodiment, the composition according to the invention may comprise one or more non-oxyalkylenated alcohols comprising at least 8 carbon atoms, and one or more monocarboxylic acid esters comprising at least 8 carbon atoms in total.

According to this embodiment, the composition according to the invention may comprise the non-oxyalkylenated alcohol(s) comprising at least 8 carbon atoms in an amount ranging from 0.01 to 10% by weight, or even from 0.02 to 5% by weight, better still from 0.05 to 2% by weight and even better still from 0.07 to 1 by weight, relative to the total weight of the composition; it may also comprise the monocarboxylic acid esters comprising at least 8 carbon atoms in an amount ranging from 0.01 to 10% by weight, or even from 0.1 to 5% by weight, better still from 0.5 to 3% by weight and even better still from 0.7 to 2% by weight relative to the total weight of the composition.

5/ Other Ingredients

Preferably, the composition according to the invention is aqueous and comprises water at a concentration preferably ranging from 40% to 95% by weight, especially from 50% to 90% by weight and better still from 60% to 85% by weight, relative to the total weight of the composition.

The composition may also comprise one or more organic solvents that are liquid at 25° C. and 1 atm., which are especially water-soluble, such as $C_1$-$C_7$ alcohols, and especially $C_1$-$C_7$ aliphatic or aromatic monoalcohols. Advantageously, the organic solvent may be chosen from ethanol and isopropanol, and mixtures thereof.

Advantageously, the composition according to the invention may also comprise one or more polyols comprising from 1 to 7 carbon atoms, especially from 2 to 6 carbon atoms, and preferably comprising 2 or 3 hydroxyl groups; mention may be made in particular of glycerol, propylene glycol and hexylene glycol, and also mixtures thereof.

When it comprises such polyol(s), the composition comprises it (them) in an amount preferably ranging from 0.1% to 20% by weight, especially from 1% to 10% by weight and better still from 2% to 8% by weight relative to the total weight of the composition.

The pH of the composition, if it is aqueous, is preferably between 3.5 and 7.5 and especially between 4.5 and 6.5.

The pH may be adjusted to the desired value by means of basifying agents or acidifying agents that are customarily used. Among the basifying agents, mention may be made of aqueous ammonia, alkanolamines, and mineral or organic hydroxides. Among the acidifying agents, mention may be made of mineral or organic acids, for instance hydrochloric acid, orthophosphoric acid or sulfuric acid, carboxylic acids, for instance acetic acid, tartaric acid, citric acid and lactic acid, and sulfonic acids.

Advantageously, the composition according to the invention may also comprise one or more nonionic surfactants, which may be chosen from alcohols, α-diols and (C1-20) alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; these compounds preferably comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-24 alkyl)glucamine derivatives, amine oxides such as (C10-14 alkyl)amine oxides or N—(C10-14 acyl) aminopropylmorpholine oxides.

Mention may also be made of nonionic surfactants of alkyl(poly)glycoside type, represented especially by the following general formula: $R_1O$—$(R_2O)_t$-$(G)_v$ in which:
  $R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
  $R_2$ represents an alkylene radical comprising 2 to 4 carbon atoms,
  G represents a sugar unit comprising 5 to 6 carbon atoms,
  t denotes a value ranging from 0 to 10 and preferably 0 to 4,
  v denotes a value ranging from 1 to 15 and preferably 1 to 4.

Preferably, the alkyl(poly)glycoside surfactants are compounds of the formula described above in which:
  $R_1$ denotes a linear or branched, saturated or unsaturated alkyl radical comprising from 8 to 18 carbon atoms,
  $R_2$ represents an alkylene radical comprising 2 to 4 carbon atoms,
  t denotes a value ranging from 0 to 3 and preferably equal to 0,
  G denotes glucose, fructose or galactose, preferably glucose;
  the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glucosides 1,4, and especially decyl glucosides and caprylyl/capryl glucosides, are most particularly preferred.

Preferentially, the nonionic surfactants are chosen from (C6-24 alkyl)(poly)glycosides, and more particularly (C8-18 alkyl)(poly)glycosides, ethoxylated C8-C30 fatty acid esters of sorbitan, polyethoxylated C8-C30 fatty alcohols and polyoxyethylenated C8-C30 fatty acid esters, these compounds preferably containing from 2 to 150 mol of ethylene oxide, and mixtures thereof.

Preferably, when they are present, the composition according to the invention comprises said nonionic surfactant(s) in an amount ranging from 0.01% to 10% by weight, especially ranging from 0.05% to 5% by weight and better still from 0.05% to 1% by weight, relative to the total weight of the composition.

The composition according to the invention may also comprise one or more additives chosen from anionic and nonionic polymers, cationic surfactants, ceramides, pseudoceramides, vitamins and provitamins including panthenol, water-soluble and liposoluble sunscreens, nacreous agents, sequestrants, solubilizers, antioxidants, antidandruff agents, anti-seborrhoeic agents, agents for preventing hair loss and/or for promoting hair regrowth, penetrants, fragrances, peptizers and preserving agents, or any other additive conventionally used in the cosmetics field. These additives may be present in the composition according to the invention in an amount ranging from 0 to 20% by weight, relative to the total weight of the composition. A person skilled in the art will take care to select these optional additives and amounts thereof so that they do not harm the properties of the compositions of the present invention.

The compositions according to the invention may advantageously be in the form of a hair composition, especially in the form of a washing hair composition, such as a shampoo, especially a conditioning shampoo.

The present invention also relates to a cosmetic process for treating, and more particularly for washing and conditioning, keratin materials, especially keratin fibres, in particular the hair, which comprises the application to said keratin materials of a composition as described above, optionally followed by a leave-on time and/or a rinsing step and/or a drying step.

The application may be performed on dry or wet hair.

The leave-on time of the composition on the keratin fibres may be from 5 seconds to 10 minutes, better still from 10 seconds to 5 minutes and even better still from 20 seconds to 2 minutes.

The invention is illustrated in greater detail in the examples that follow, in which, unless otherwise mentioned, the amounts indicated are expressed as weight percentages of active material (AM) of product relative to the total weight of the composition.

EXAMPLE 1

The shampoo composition below according to the invention was prepared.

| Composition | weight % of AM |
|---|---|
| Sodium lauryl ether sulfate containing 2 EO | 7.35 |
| Sodium lauryl sulfoacetate | 0.7 |
| Disodium lauryl ether sulfosuccinate | 1.8 |
| Cocamidopropyl betaine | 13.1 |
| Polyquaternium-6 (Merquat 100) | 0.4 |
| Octyldodecanol | 0.1 |
| Isopropyl myristate | 1 |
| PEG-55 propylene glycol oleate | 0.25 |
| Glycerol | 2 |
| Hexylene glycol | 1.7 |
| Propylene glycol | 0.7 |
| NaCl | 3.3 |
| pH agent | qs pH 5.3 |
| Water | qs 100% |
| Anionic SA/amphoteric SA ratio | 0.75 |

A clear, colourless shampoo is obtained, which remains stable on storage (2 months at 45° C.), without phase separation or decantation.

It affords nutrition and styling to the hair, in particular to fine hair, without making it lank.

EXAMPLE 2

The compositions according to the invention or the comparative compositions below were prepared (weight % of AM).

| Composition | Invention 2 | Invention 3 | Invention 4 |
|---|---|---|---|
| Sodium lauryl ether sulfate containing 2 EO | 7.35 | 7.35 | 7.35 |
| Sodium lauryl sulfoacetate | 0.7 | 0.7 | 0.7 |
| Disodium lauryl ether sulfosuccinate | 1.8 | 1.8 | 1.8 |
| Cocamidopropyl-betaine | 13.1 | 13.1 | 13.1 |
| Polyquaternium-6 (Merquat 100) | 0.4 | 0.4 | 0.4 |
| Octyldodecanol | 0.2 | 0.1 | 0.1 |
| PPG-5-Ceteth-20 | 0.4 | — | 0.2 |
| PEG-55 propylene glycol oleate | 0.25 | 0.25 | 0.25 |
| Glycerol | 2% | 2% | 2% |
| Hexylene glycol | 1.7% | 1.7% | 1.7% |
| Propylene glycol | 0.7% | 0.7% | 0.7% |
| NaCl | 2.9% | 2.9% | 2.9% |
| pH agent | qs pH 5.3 | qs pH 5.3 | qs pH 5.3 |
| Water | qs 100% | qs 100% | qs 100% |
| Anionic SA/amphoteric SA ratio | 0.75 | 0.75 | 0.75 |
| Appearance of the composition | Clear | Clear | Clear |

| Composition | Invention 5 | Invention 6 | Invention 7 |
|---|---|---|---|
| Sodium lauryl ether sulfate containing 2 EO | 7.35 | 7.35 | 7.35 |
| Sodium lauryl sulfoacetate | 0.7 | — | 0.7 |
| Disodium lauryl ether sulfosuccinate | 1.8 | — | 1.8 |
| Cocamidopropyl-betaine | 13.1 | 13.1 | 13.1 |
| Polyquaternium-6 (Merquat 100) | 0.4 | 0.4 | 0.4 |
| 2-Decyl-1-tetradecanol | 0.2% | — | — |
| Isopropyl myristate | — | 1% | 1% |
| PEG-55 propylene glycol oleate | 0.25% | 0.25% | 0.25% |
| Glycerol | 2% | 2% | 2% |
| Hexylene glycol | 1.7% | 1.7% | 1.7% |
| Propylene glycol | 0.7% | 0.7% | 0.7% |
| NaCl | 2.9% | 3.4% | 3.4% |
| pH agent | qs pH 5.3 | qs pH 5.3 | qs pH 5.3 |
| Water | qs 100% | qs 100% | qs 100% |
| Anionic SA/amphoteric SA ratio | 0.75 | 0.56 | 0.75 |
| Appearance of the composition | Clear | Clear | Clear |

| Composition | Control | Comparative 1 | Comparative 2 |
|---|---|---|---|
| Sodium lauryl ether sulfate containing 2 EO | 7.35% AM | 7.35% AM | 7.35% AM |
| Cocamidopropyl-betaine | 13.1% AM | 13.1% AM | 13.1% AM |
| Polyquaternium-6 (Merquat 100) | 0.4% AM | 0.4% AM | 0.4% AM |
| Olive oil | — | 0.3% | — |
| Sweet almond (Prunus amygdalus dulcis) oil | — | — | 0.3% |
| PEG-55 propylene glycol oleate | 0.25% | 0.25% | 0.25% |
| PEG-60 Hydrogenated castor oil | — | 0.2% AM | 0.2% AM |
| Glycerol | 2% | 2% | 2% |
| Hexylene glycol | 1.7% | 1.7% | 1.7% |
| Propylene glycol | 0.7% | 0.7% | 0.7% |
| NaCl | 3.4% | 3.4% | 3.4% |
| pH agent | qs pH 5.3 | qs pH 5.3 | qs pH 5.3 |
| Water | qs 100% | qs 100% | qs 100% |
| Anionic SA/amphoteric SA ratio | 0.56 | 0.56 | 0.56 |
| Appearance of the composition | Clear | Cloudy | Cloudy |

With compositions 2 to 7 according to the invention, a clear shampoo that is stable on storage is obtained, which provides nutrition and styling to the hair, without making it lank.

The control shampoo which does not comprise any liquid fatty substance according to the invention is also clear, but it does not provide any nutrition or styling to the hair.

The comparative shampoos 1 and 2 which contain plant oils are, for their part, cloudy even from the moment of manufacture.

The invention claimed is:

1. A cosmetic composition comprising:
    one or more anionic surfactants present in a total amount ranging from 7% to 15% by weight relative to the total weight of the composition,
    one or more amphoteric surfactants,
    one or more cationic polymers with a cationic charge density of greater than or equal to 4 meq./g chosen from cyclopolymers of alkyldiallylamine or of dialkyldiallylammonium, containing, as main constituent of the chain, units corresponding to formula (I) or (II):

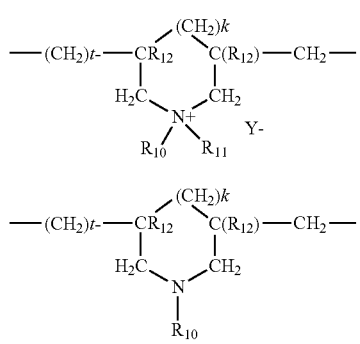

in which
k and t are equal to 0 or 1, the sum k+t being equal to 1;
R12 denotes a hydrogen atom or a methyl radical;
R10 and R11, independently of each other, denote a C1-C6 alkyl group, a C1-C5 hydroxyalkyl group, a C1-C4 amidoalkyl group; or alternatively R10 and R11 may denote, together with the nitrogen atom to which they are attached, a heterocyclic group; R10 and R11, independently of each other, denote a C1-C4 alkyl group; and
Y$^-$ is an anion, and
one or more liquid fatty substances chosen from non-oxyalkylenated alcohols comprising at least 8 carbon atoms, monocarboxylic acid esters comprising at least 8 carbon atoms, and mixtures thereof.

2. The composition according to claim 1, wherein the one or more anionic surfactants is chosen, alone or as a mixture, from:
    C6-C30 alkyl sulfates;
    C6-C30 alkyl ether sulfates; comprising from 2 to 20 ethylene oxide units,
    C6-C30 alkylsulfosuccinates;
    C6-C30 alkyl ether sulfosuccinates; comprising from 2 to 20 ethylene oxide units,
    C6-C30 alkylsulfoacetates;
    polyoxyalkylenated C6-C24 alkyl ether carboxylic acids, comprising from 2 to 15 alkylene oxide groups;
    polyoxyalkylenated C6-C24 alkylamido ether carboxylic acids, comprising from 2 to 15 alkylene oxide groups; and
    salts thereof.

3. The composition according to claim 1, comprising:
    at least one anionic surfactant chosen from C6-C30 alkyl ether sulfates, comprising from 2 to 20 ethylene oxide units,
    at least one anionic surfactant chosen from C6-C30 alkyl ether sulfosuccinates, comprising from 2 to 20 ethylene oxide units, and
    optionally, at least one anionic surfactant chosen from C6-C30 alkylsulfoacetates.

4. The composition according to claim 1, wherein the one or more amphoteric surfactants is chosen from:
    (C8-C20)alkylbetaines, sulfobetaines, alkyl(C8-C20)sulfobetaines, (C8-C20)alkylamido(C1-C6)alkylbetaines and (C8-C20)alkylamido(C1-C6)alkylsulfobetaines;
    optionally quaternized secondary or tertiary aliphatic amine derivatives of formulae (A1) and (A2) below:

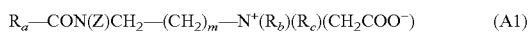

in which:
$R_a$ represents a C10-C30 alkyl or alkenyl group derived from an acid $R_a$—COOH,
$R_b$ represents a β-hydroxyethyl group,
$R_c$ represents a carboxymethyl group;
m is equal to 0, 1 or 2,
Z represents a hydrogen atom or a hydroxyethyl group or a carboxymethyl group,

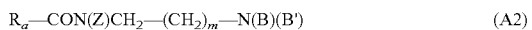

in which:
B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom,
B' represents —(CH$_2$)$_z$—Y', with z=1 or 2, and Y' representing —COOH, —COOZ', —CH$_2$—CHOH—SO$_3$H or —CH$_2$—CHOH—SO$_3$Z',
m' is equal to 0, 1 or 2,
Z represents a hydrogen atom or a hydroxyethyl group or a carboxymethyl group,
Z' represents an ion derived from an alkali metal or alkaline-earth metal, or an ion derived from an organic amine; and
$R_{a'}$ represents a C10-C30 alkyl or alkenyl group of an acid $R_{a'}$COOH;
compounds of formula (A3):

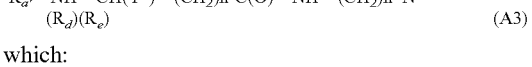

in which:
$R_{a''}$ represents a C10-C30 alkyl or alkenyl group derived from an acid
$R_{a''}$—C(O)OH, which is present in hydrolysed linseed oil or coconut oil;
Y″ represents the group —C(O)OH, —C(O)OZ″, —CH$_2$—CH(OH)—SO$_3$H or the group —CH$_2$—CH(OH)—SO$_3$—Z″, with Z″ representing a cationic counterion derived from an alkali metal or alkaline-earth metal, or an ion derived from an organic amine;
$R_d$ and $R_e$, independently of each other, represent a C1-C4 alkyl or hydroxyalkyl radical; and
n and n', independently of each other, denote an integer ranging from 1 to 3.

5. The composition according to claim 1, wherein the one or more amphoteric surfactants is chosen from (C8-C20)alkylbetaines, (C8-C20)alkylamido(C1-C6)alkylbetaines, (C8-C20)alkylamphodiacetates, and mixtures thereof.

6. The composition according to claim 1, comprising said amphoteric surfactant(s) in an amount ranging from 1% to 25% by weight relative to the total weight of the composition.

7. The composition according to claim 1, comprising the anionic surfactant(s) and the amphoteric surfactant(s) in a total amount such that the weight ratio between anionic surfactant(s) and amphoteric surfactant(s) is less than or equal to 1.

8. The composition according to claim 1 wherein the cationic charge density of the one or more cationic polymer is greater than or equal to 5 meq./g.

9. The composition according to claim 1, wherein $Y^-$ in the one or more cationic polymers with a charge density of greater than or equal to 4 meq/g is bromide, chloride, acetate, borate, citrate, tartrate, bisulfate, bisulfite, sulfate or phosphate.

10. The composition according to claim 1, wherein the one or more cationic polymers with a charge density of greater than or equal to 4 meq./g, is chosen from:
    homopolymers of dimethyldiallylammonium salts, and copolymers of diallyldimethylammonium salts and of acrylamide;
    mixtures thereof.

11. The composition according to claim 1, wherein the weight % of the cationic polymer(s) with a cationic charge density of greater than or equal to 4 meq./g is from 0.01% to 10% by weight relative to the total weight of the composition.

12. The composition according to claim 1, wherein at least one non-oxyalkylenated alcohol comprising at least 8 carbon atoms is present as the one or more liquid fatty substances and is chosen from compounds of the structure R—OH in which R denotes a saturated, branched C8-C30, alkyl group, or a linear or branched, C8-C30 alkenyl group comprising 1 to 3 double bonds.

13. The composition according to claim 1, wherein at least one monocarboxylic acid ester comprising at least 8 carbon atoms is present as the one or more liquid fatty substances and is chosen from liquid esters of monoalcohols or of polyols with monocarboxylic acids comprising from 8 to 32 carbon atoms.

14. The composition according to claim 13, wherein the at least one monocarboxylic acid ester is chosen from esters of a C6-C24 monocarboxylic acid and of a C2-C20 alcohol, at least one from among the acid and the alcohol being branched or unsaturated.

15. The composition according to claim 1, wherein a weight % of the liquid fatty substances chosen from non-oxyalkylenated alcohols comprising at least 8 carbon atoms, monocarboxylic acid esters comprising at least 8 carbon atoms, and mixtures thereof, is from 0.01% to 20% by weight relative to the total weight of the composition.

16. The composition according to claim 1, wherein said liquid non-oxyalkylenated alcohol(s) comprising at least 8 carbon atoms is present in an amount ranging from 0.01% to 10% by weight relative to the total weight of the composition; and
    said liquid monocarboxylic acid ester(s) comprising at least 8 carbon atoms is present in an amount ranging from 0.01% to 10% by weight, relative to the total weight of the composition.

17. The composition according to claim 1, further comprising water in a content ranging from 40% to 95% by weight relative to the total weight of the composition.

18. The composition according to claim 1, further comprising one or more polyols comprising from 1 to 7 carbon atoms in an amount ranging from 0.1 to 20% by weight relative to the total weight of the composition.

19. The composition according to claim 1, further comprising one or more nonionic surfactants in an amount ranging from 0.01% to 10% by weight relative to the total weight of the composition.

20. The composition according to claim 1 wherein the composition is transparent.

21. A cosmetic process for washing and/or conditioning keratin materials comprising applying to said materials a composition according to claim 1.

* * * * *

UNITED STATES PATENT AND TRADEMARK OFFICE
CERTIFICATE OF CORRECTION

PATENT NO. : 11,376,204 B2
APPLICATION NO. : 16/301635
DATED : July 5, 2022
INVENTOR(S) : Thomas et al.

It is certified that error appears in the above-identified patent and that said Letters Patent is hereby corrected as shown below:

In the Claims

In Column 20, Claim 4, Line 25, delete "$R_a$-CON(Z)CH$_2$-(CH$_2$)$_m$-N(B)(B')" and insert -- $R_{a'}$-CON(Z)CH$_2$-(CH$_2$)$_{m'}$-N(B)(B') --, therefor.

In Column 20, Claim 4, Lines 44-45, delete "$R_a$" and insert -- $R_{a"}$ --, therefor.

In Column 21, Claim 9, Line 11, delete "meq/g" and insert -- meq./g --, therefor.

In Column 21, Claim 10, Line 19, insert -- and -- after "acrylamide;".

Signed and Sealed this
Twenty-ninth Day of November, 2022

Katherine Kelly Vidal
*Director of the United States Patent and Trademark Office*